US008603606B2

(12) United States Patent
Stuke et al.

(10) Patent No.: US 8,603,606 B2
(45) Date of Patent: Dec. 10, 2013

(54) PREVENTING ADHESION BETWEEN NANOSTRUCTURES

(75) Inventors: Michael Josef Stuke, Palo Alto, CA (US); Zhiyong Li, Redwood City, CA (US); Shih-Yuan Wang, Palo Alto, CA (US); Fung Suong Ou, Palo Alto, CA (US); Min Hu, Sunnyvale, CA (US); Wei Wu, Palo Alto, CA (US); Lars Helge Thylen, Huddinge (SE)

(73) Assignee: Hewlett-Packard Development Company, L.P., Houston, TX (US)

( * ) Notice: Subject to any disclaimer, the term of this patent is extended or adjusted under 35 U.S.C. 154(b) by 552 days.

(21) Appl. No.: 12/916,239

(22) Filed: Oct. 29, 2010

(65) Prior Publication Data

US 2012/0107569 A1    May 3, 2012

(51) Int. Cl.
*B32B 3/00* (2006.01)
*B05D 7/00* (2006.01)

(52) U.S. Cl.
USPC ........... 428/141; 428/172; 427/404; 427/331; 427/372.2; 427/547

(58) Field of Classification Search
None
See application file for complete search history.

(56) References Cited

U.S. PATENT DOCUMENTS

| 7,416,019 | B2 | 8/2008 | Osiander et al. | |
| 7,880,318 | B1* | 2/2011 | Kamins et al. | 257/798 |
| 2007/0086001 | A1* | 4/2007 | Islam et al. | 356/301 |
| 2007/0220713 | A1 | 9/2007 | Choy et al. | |
| 2008/0199663 | A1 | 8/2008 | Burmeister | |
| 2010/0003421 | A1 | 1/2010 | Ebels et al. | |
| 2011/0188034 | A1* | 8/2011 | Stuke et al. | 356/301 |
| 2011/0267606 | A1* | 11/2011 | Ou et al. | 356/301 |

FOREIGN PATENT DOCUMENTS

WO    WO-2007/052260    5/2007

OTHER PUBLICATIONS

Zheng, Haidong et al., "UV-Induced Wettability Change of Teflon-modified ZnO Nanorod Arrays on LiNbO3 Substrate", *IEEEXplore Digital Library*, Feb. 25-29, 2008. pp. 218-221, <http://ieeexplore.ieee.org/Xplore/login.jsp.

Khudhayer, Wisam J., et al., "Hydrophobic Metallic Nanorods coated with Teflon Nanopatches by Glancing Angle Deposition" *IOPScience*. Jun. 16, 2009; vol. 20 http://iopscience.iop.org/0957-4484/20/27/275302.

* cited by examiner

*Primary Examiner* — Maria Veronica Ewald
*Assistant Examiner* — Nicole T Gugliotta

(57) ABSTRACT

A device for Surface Enhanced Raman Scattering (SERS). The device includes a plurality of nanostructures protruding from a surface of a substrate, a SERS active metal disposed on a portion of said plurality of nanostructures, and a low friction film disposed over the plurality of nanostructures and the SERS active metal. The low friction film is to prevent adhesion between the plurality of nanostructures.

15 Claims, 3 Drawing Sheets

PREVENTING ADHESION BETWEEN NANOSTRUCTURES

GOVERNMENT INTEREST

Subject matter described herein was made with government support under Contract No. HR0011-09-3-0002 awarded by Defense Advanced Research Projects Agency. The government has certain rights in the described subject matter.

BACKGROUND

Surface Enhanced Raman Scattering (SERS) is a technique using Raman scattering for enhancing the detection of molecular species through the excitation of Plasmon modes and their coupling to molecular vibrational modes. In other words, Raman scattering is the inelastic scattering of photons that can provide vibrational fingerprints of molecules.

Nanostructures on a substrate where the detection of molecular species takes place affects the Raman scattering. In particular, when the nanostructures are adhered together, the Raman scattering can be negatively affected.

The drawings referred to in this description should be understood as not being drawn to scale except if specifically noted.

DESCRIPTION

Reference will now be made in detail to examples of the present technology, examples of which are illustrated in the accompanying drawings. While the technology will be described in conjunction with various example(s), it will be understood that they are not intended to limit the present technology to these examples. On the contrary, the present technology is intended to cover alternatives, modifications and equivalents, which may be included within the spirit and scope of the various examples as defined by the appended claims.

Furthermore, in the following description of examples, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present examples.

Figure 1:
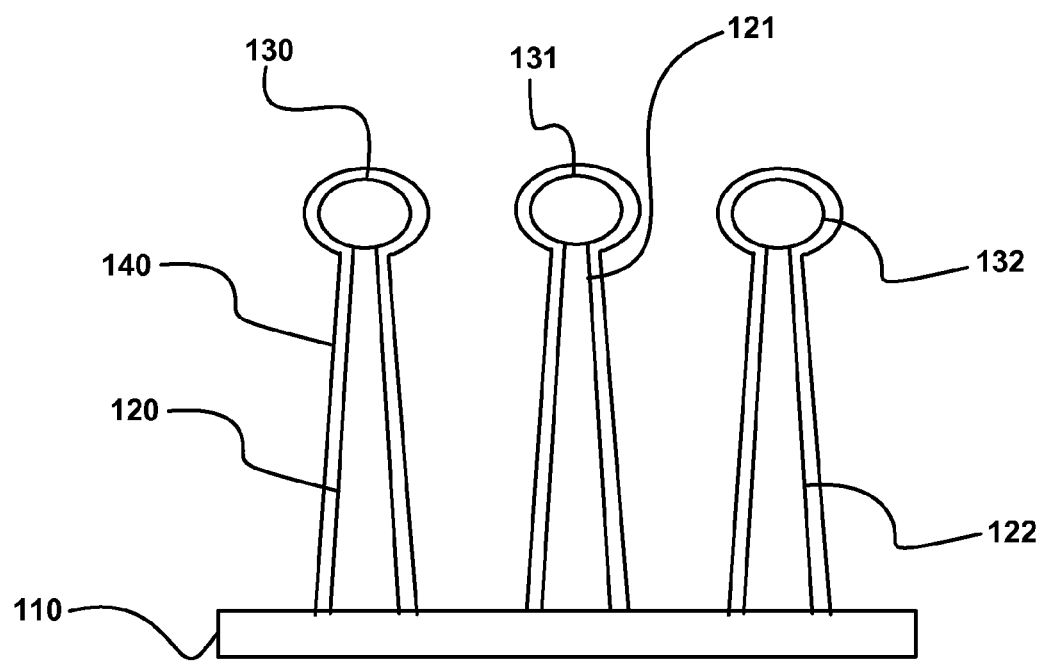
FIGS. 1 and 2 illustrate examples of a device for SERS, in accordance with examples of the present technology.

FIG. 1 depicts device 100 for SERS, in accordance with an example of the present technology. Device 100 includes substrate 110, nanostructures 120-122, SERS active metal 130-132 and low friction film 140.

Nanostructures 120-122 are disposed on substrate 110. It should be appreciated that any number of nanostructures are disposed in various orientations on substrate 110. In various examples, the shapes of the nanostructures 120-122 can be, but are not limited to, conical, cylindrical and the like. It should be appreciated nanostructures 120-122 can be any shape that facilitates in the enhancement of Raman scattering.

In one example, nanostructures 120-122 are flexible, such that nanostructures 120-122 may come into contact with neighboring nanostructures.

SERS active metals 130-132 are disposed at least on a portion of nanostructures 120-122. In general, SERS active metals are metals that help provide for the enhancement of Raman scattering during SERS.

In one example, SERS active metals 130-132 are disposed on a tip portion of nanostructures 120-122. It should be appreciated that a SERS active metal can be disposed on nanostructures in any fashion to facilitate in enhancing Raman scattering. For example, SERS active metal can be deposited as a uniform thin layer on all of the nanostructures. SERS active metals 130-132, can be, but are not limited to, silver, gold, platinum or copper.

Low friction film 140 is to prevent adhesion between nanostructures 120-122. In contrast, in conventional technology, oftentimes nanostructures in close proximity to one another adhere to one another. Accordingly, SERS is negatively affected. Moreover, long term use of SERS devices is also negatively affected.

The adhesion between nanostructures is often due to van der Waals forces between the nanostructures. Additionally, nanostructures may be brought together via microcapillary forces.

Low friction film 140 is disposed over SERS active metals 130-132 and nanostructures 120-122. In one example, low friction film 140 has a thickness of 2 nanometers or less.

Low friction film 140 can be, but is not limited to, $CF_4$, $C_2F_4$, and diamond-like carbon. It should be appreciated that low friction film is any film that includes low interaction forces and is able to prevent adhesion between nanostructures. In particular, low friction film is an film that prevents adhesion due to van der Waals forces.

Low friction film 140 may be deposited on nanostructures 120-122 and SERS active metals 130-132 in a variety of ways. For example, low friction film 140 may be deposited by, but not limited to, vapor deposition, chemical vapor deposition (CVD), plasma CVD, molecule self assembly, atomic layer deposition, and the like.

Figure 2:
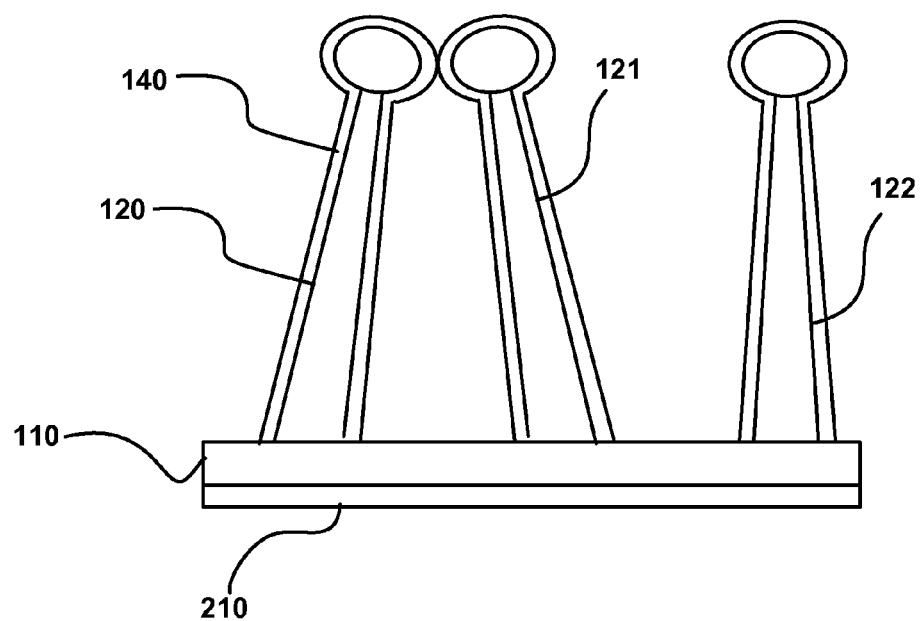

FIG. 2 depicts device 200 for SERS, in accordance with an example of the present technology. Device 200 is similar to device 100, as described above. However, device 200 includes nanostructure detacher 210.

Nanostructure detacher 210 is to detach nanostructures that are attached to one another. For example, if nanostructures 120 and 121 are adhered together due to van der Waals forces, nanostructure detacher 210 facilitates in detaching nanostructures 120 and 121. It should be appreciated that nanostructure detacher 210 can be disposed at any location with respect to devices 100 or 200 such that it is able to facilitate in detaching nanostructures.

In one example, nanostructure detacher 210 is a piezoelectric substrate to excite attached nanostructures to a resonant vibration frequency. Once the nanostructures are detached from one another, the resonant frequency is shifted or reduced. Also, the amplitude may be limited, because once the nanostructures are detached, their resonant vibration frequency will be shifted and the nanostructures cannot absorb any more energy from the vibration excitation source.

In another example, nanostructure detacher 210 is a heat source that thermally expands the attached nanostructures. For example, the thermal expansion of the attached nanostructures can overcome van der Waals forces and result in detaching of the nanostructures.

In a further example, nanostructure detacher 210 is a magnet (e.g., electro magnet) that provides a magnetic field. For example, a magnetic field provided to the attached nanostructure can facilitate in the attached nanostructures to overcome van der Waals forces and result in detaching of the nanostructures.

Figure 3:
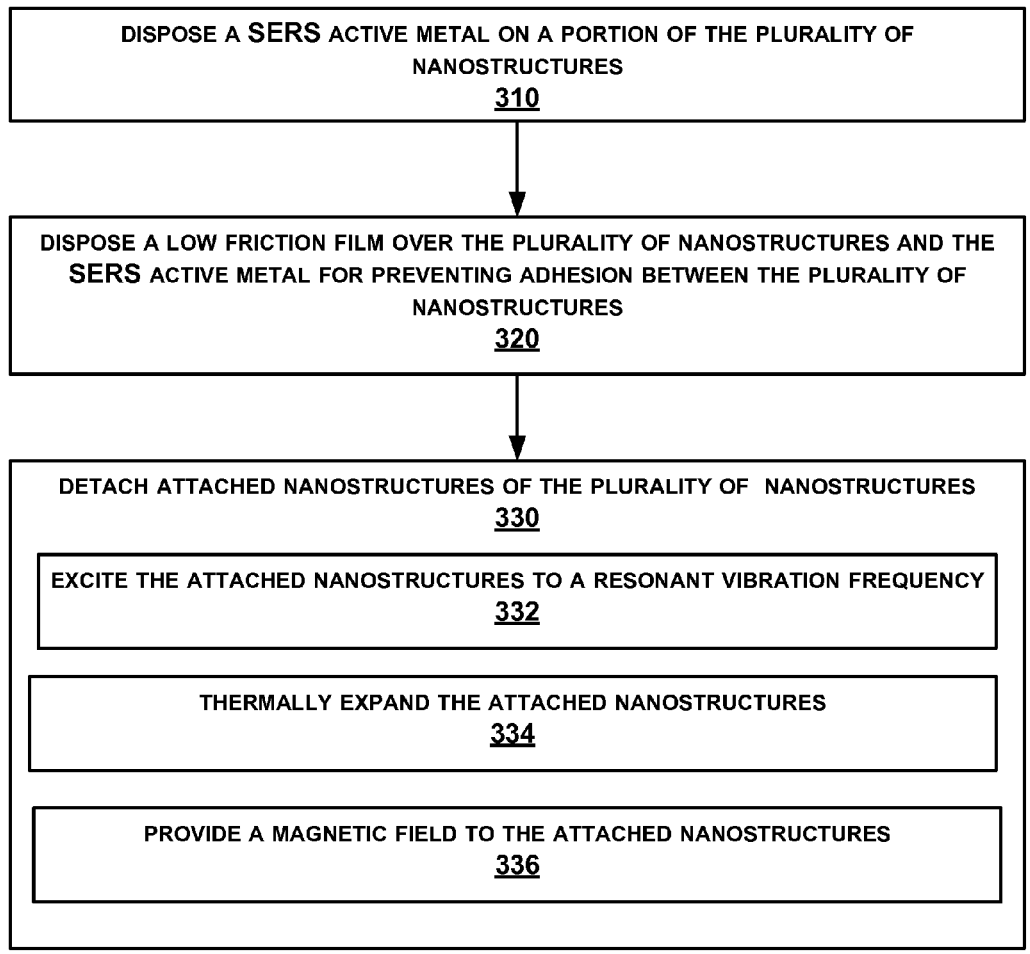
FIG. 3 illustrates an example of a method for preventing adhesion between nanostructures, in accordance with an example of the present technology.

FIG. 3 depicts a method 300 for preventing adhesion between nanostructures.

At 310, a SERS active metal is disposed on a portion of the plurality of nanostructures. For example, gold is disposed on a tip portion of nanostructures 120-122.

At 320, a low friction film is disposed over the plurality of nanostructures and the SERS active metal, wherein the low friction film is for preventing adhesion between the plurality of nanostructures. For example, low friction film 140 is uniformly disposed over nanostructures 120-122 and SERS active metals 130-132 to prevent adhesion between nanostructures 120-122 due to van der Waals forces. In various examples, the low friction film can be, but is not limited to, $CF_4$, $C_2F_4$, and diamond-like carbon.

At 330, attached nanostructures are detached from one another. For example, nanostructures 120 and 121 are adhered to one another due to van der Waals forces, as depicted in FIG. 2. However, nanostructure detacher 210 facilitates in detaching nanostructures 120 and 121. Accordingly, nanostructures 120 and 121 are not attached to one another, as depicted in FIG. 1.

In one example, at 332, the attached nanostructures are excited to a resonant vibration frequency. For example, a vibration excitation source (e.g., piezoelectric substrate) excites attached nanostructures 120 and 121 to a resonant vibration frequency to facilitate in the detaching of nanostructures 120 and 121.

In another example, at 334, the attached nanostructures are thermally expanded. For example, a heat source provides heat to attached nanostructures 120 and 121 to facilitate in the detaching of nanostructures 120 and 121.

In a further example, at 336, a magnetic field is provided to the attached nanostructures. For example, attached nanostructures 120 and 121 are provided with a magnetic field to facilitate in the detaching of nanostructures 120 and 121.

Various examples of the present technology are thus described. While the present technology has been described in particular examples, it should be appreciated that the present technology should not be construed as limited by such examples, but rather construed according to the following claims.

The invention claimed is:

1. A device for Surface Enhanced Raman Scattering (SERS), said device comprising:
    a plurality of nanostructures protruding from a surface of a substrate;
    a SERS active metal disposed on a portion of said plurality of nanostructures; and
    a low friction film disposed over said plurality of nanostructures and said SERS active metal, wherein said low friction film is to prevent adhesion between said plurality of nanostructures.

2. The device of claim 1, wherein said SERS active metal is selected from a group consisting of: silver, gold, platinum and copper.

3. The device of claim 1, wherein said SERS active metal is disposed on a tip of said plurality of nanostructures.

4. The device of claim 1, wherein said low friction film comprises:
    a thickness less than two nanometers.

5. The device of claim 1, wherein said low friction film is selected from a group consisting of: $CF_4$, $C_2F_4$, and diamond-like carbon.

6. The device of claim 1, further comprising:
    a nanostructure detacher to detach attached nanostructures of said plurality of nanostructures.

7. The device of claim 6, wherein said nanostructure detacher comprises:
    a piezoelectric substrate.

8. The device of claim 6, wherein said nanostructure detacher comprises:
    a heater for generating thermal expansion of said attached nanostructures.

9. The device of claim 6, wherein said nanostructure detacher comprises:
    a magnet for generating a magnetic field to said attached nanostructures.

10. A method for preventing adhesion between a plurality of nanostructures, said method comprising:
    disposing a SERS active metal on a portion of said plurality of nanostructures; and
    disposing a low friction film over said plurality of nanostructures and said SERS active metal for preventing adhesion between said plurality of nanostructures.

11. The method of claim 10, wherein said disposing a low friction film over said plurality of nanostructures and said SERS active metal comprises:
    disposing said low friction film over said plurality of nanostructures and said SERS active metal, wherein said low friction film is selected from a group consisting of: $CF_4$, $C_2F_4$, and diamond-like carbon.

12. The method of claim 10, further comprising:
    detaching attached nanostructures of said plurality of nanostructures.

13. The method of claim 12, wherein said detaching attached nanostructures of said plurality of nanostructures comprises:
    exciting said attached nanostructures to a resonant vibration frequency.

14. The method of claim 12, wherein said detaching attached nanostructures of said plurality of nanostructures comprises:
    thermally expanding said attached nanostructures.

15. The method of claim 12, wherein said detaching attached nanostructures of said plurality of nanostructures comprises:
    providing a magnetic field to said attached nanostructures.

* * * * *